(12) United States Patent
Baba et al.

(10) Patent No.: US 8,097,246 B2
(45) Date of Patent: Jan. 17, 2012

(54) PROMOTER OF DIFFERENTIATION AND KERATINIZATION OF EPIDERMIC CELL AND FUNCTIONAL BEVERAGE/FOOD FOR PROMOTION OF KERATINIZATION OF EPIDERMIS

(75) Inventors: Hidehiko Baba, Sagamihara (JP); Akihiro Masuyama, Sagamihara (JP); Chiaki Yoshimura, Yokohama (JP)

(73) Assignee: Calpis Co., Ltd., Tokyo (JP)

(*) Notice: Subject to any disclaimer, the term of this patent is extended or adjusted under 35 U.S.C. 154(b) by 949 days.

(21) Appl. No.: 11/993,111

(22) PCT Filed: Jun. 23, 2006

(86) PCT No.: PCT/JP2006/312578
§ 371 (c)(1),
(2), (4) Date: Mar. 17, 2008

(87) PCT Pub. No.: WO2006/137513
PCT Pub. Date: Dec. 28, 2006

(65) Prior Publication Data
US 2010/0166877 A1   Jul. 1, 2010

(30) Foreign Application Priority Data

Jun. 24, 2005  (JP) .................................. 2005-184994

(51) Int. Cl.
*C12P 1/04* (2006.01)
*A61K 35/20* (2006.01)

(52) U.S. Cl. .................... 424/93.46; 424/535; 424/94.1; 435/170

(58) Field of Classification Search ................. 424/93.1, 424/93.46, 535; 435/170
See application file for complete search history.

(56) References Cited

U.S. PATENT DOCUMENTS

| | | | |
|---|---|---|---|
| 6,284,243 B1 * | 9/2001 | Masuyama et al. | ........ 424/93.45 |
| 6,534,304 B1 | 3/2003 | Yamamoto et al. | |
| 6,596,301 B1 | 7/2003 | Masuyama et al. | |
| 2003/0108617 A1 | 6/2003 | Leithe et al. | |
| 2004/0013706 A1 | 1/2004 | Baur et al. | |

FOREIGN PATENT DOCUMENTS

| CN | 1279712 A | 1/2001 |
|---|---|---|
| JP | 10-45610 | 2/1998 |
| JP | 10-045610 A | 2/1998 |
| JP | 11-98978 | 4/1999 |
| JP | 2000-239175 A | 5/2000 |
| JP | 11-098978 A | 8/2002 |
| JP | 2002-241289 A | 8/2002 |
| JP | 2004-501199 | 1/2004 |
| JP | 2004-501199 A | 1/2004 |
| JP | 2004-510740 | 4/2004 |
| JP | 2004-510740 A | 4/2004 |
| JP | 2005-206578 A | 8/2005 |
| WO | WO 2005/063196 A1 | 7/2005 |

OTHER PUBLICATIONS

English Translation of International Preliminary Report on Patentability.
Shun Arakatsu, "Nyusankin o Riyoshita Kinosei Keshohin Shokuhin no Kaihatsu Kenkyu Doko", Foods & Food Ingredients Journal of Japan, vol. 209, No. 9, 2004, p. 780-792.
Baumgartner M. et al., Controlled Trials Investigating the Use of One Partially Hydrolyzed Whey Formula for Dietary Prevention of Atopic Manifestations Until 60 Months of Age: An Overview Using Meta-Analytical Techniques, Nutrition Research, vol. 18, No. 8, 1998, p. 1425-1442.

* cited by examiner

*Primary Examiner* — Ruth Davis
(74) *Attorney, Agent, or Firm* — Sughrue Mion, PLLC

(57) ABSTRACT

The invention provides functional food and beverage that produce, through oral intake, a promotive effect on normal epidermal keratinization, and an epidermal differentiation and keratinization promoter for use in such functional food and beverage. The epidermal differentiation and keratinization promoter of the present invention contains, as an active component, fermented milk whey obtained by fermentation of milk with bacteria including lactic acid bacteria, such as *Latobacillus helveticus*. The functional food and beverage for promoting epidermal keratinization of the present invention contains the epidermal differentiation and keratinization promoter.

6 Claims, 3 Drawing Sheets

PROMOTER OF DIFFERENTIATION AND KERATINIZATION OF EPIDERMIC CELL AND FUNCTIONAL BEVERAGE/FOOD FOR PROMOTION OF KERATINIZATION OF EPIDERMIS

FIELD OF ART

The present invention relates to an epidermal differentiation and keratinization promoter and functional food and beverage for promoting epidermal keratinization, which are effective in remedying various skin troubles in dry or rough skin, or in a group of various skin disorders accompanied by parakeratosis, such as psoriasis or xeroderma, by promoting differentiation of epidermal cells to promote, in turn, normal epidermal keratinization.

BACKGROUND ART

Epidermis, which is the outermost layer of skin tissues, is directly exposed to the surrounding environment, and thus is prone to damage by various physical or chemical stimuli. The epidermal cells are continuously replaced as they are born in the lowest layer of the epidermis, the basal layer, and rise toward the outer layer. This replacement is called epidermal turnover. In this process, the epidermal cells undergo four stages of differentiation, i.e., basal cells, spinous cells, granule cells, and corneocytes, and are finally desquamated from the skin surface. It usually takes about 14 days for the basal cells to be keratinized into corneocytes, and about another 14 days for the corneocytes to be desquamated as grime. Thus the epidermis constantly repeat turnover in total of a 4- to 6-week cycle.

The corneocytes of healthy epidermis are stratified in about 15 layers to form a stratum corneum. This stratum corneum has excellent barrier function to prevent evaporation of moisture within the body, and to prevent invasion by foreign substances, such as foreign antigen, or transmission of external stimuli into the body, to thereby play an important role in biophylaxis. However, in patients with various skin disorders, such as atopic dermatitis, xeroderma, or psoriasis, formation of a healthy stratum corneum is disturbed. Abnormality of the formation of stratum corneum including parakeratosis, causes depression in skin barrier function to disadvantageously allow evaporation of moisture, invasion by foreign substances, or transmission of external stimuli into the body, which is believed to lead to skin dryness, or induction or deterioration of various skin disorders. Further, when the turnover is disturbed and the keratinization does not proceed smoothly, the stratum corneum of the skin becomes thicker to cause skin roughness, such as dryness or stiffening of the skin surface. Thus keratonosis poses a problem also from the cosmetic point of view.

In order to relieve such skin disorders or to maintain healthy skin conditions, there is proposed some methods for remedying skin troubles with a particular component. For example, Patent Publication 1 proposes to add a silicic acid-related substance to cosmetics or the like in expectation of an epidermal keratinization promoting effect. Researches for components having such an effect have been made in the field of cosmetics and skin preparations intended for external use, but no active component has been identified that is applicable to the field of food and beverage. It may be conceivable to use the above-mentioned skin preparations for external use in food and beverage, but it still remains unknown what effect may be achieved when they are actually used.

Patent Publication 1: Japanese Patent No. 3227378

SUMMARY OF THE INVENTION

It is an object of the present invention to provide functional food and beverage that produce, through oral intake, a promotive effect on normal epidermal keratinization, and an epidermal differentiation and keratinization promoter for use in such functional food and beverage.

According to the present invention, there is provided an epidermal differentiation and keratinization promoter comprising, as an active component, fermented milk whey obtained by fermentation of milk with bacteria including lactic acid bacteria.

According to the present invention, there is also provided functional food and beverage for promoting epidermal keratinization, comprising the above epidermal differentiation and keratinization promoter.

According to the present invention, there is also provided use of fermented milk whey obtained by fermentation of milk with bacteria including lactic acid bacteria for the manufacture of an epidermal differentiation and keratinization promoter, or of functional food and beverage for promoting epidermal keratinization.

The active component of the epidermal differentiation and keratinization promoter and the functional food and beverage for promoting epidermal keratinization, is fermented milk whey, of which safety has been confirmed through oral intake. Thus, an excellent promoting effect on epidermal keratinization may be achieved by the oral route with safety, and continuous intake may be expected to provide suppression of skin dryness or roughness caused by change of the seasons or climate, and improvement in symptoms of various skin disorders characterized by parakeratosis, such as atopic dermatitis, xeroderma, or psoriasis.

PREFERRED EMBODIMENTS OF THE INVENTION

Figure 1:
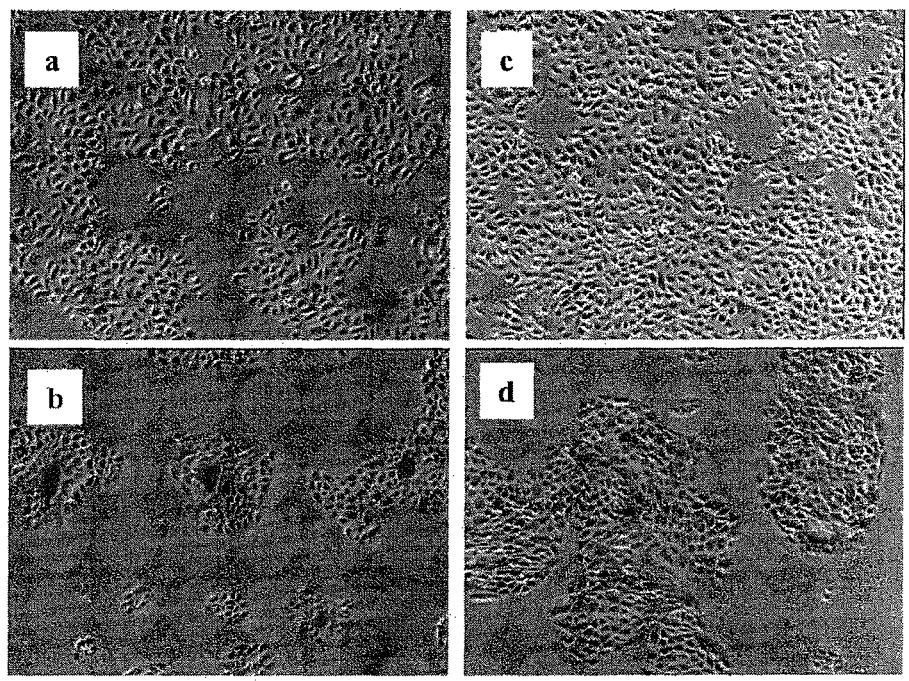
FIG. 1 is a photocopy of a micrograph showing the result of analysis of expression of differentiation marker proteins, conducted in Example 1.

The present invention will now be explained in detail.

The epidermal differentiation and keratinization promoter according to the present invention contains, as an active component, fermented milk whey obtained by fermentation of milk with bacteria including lactic acid bacteria.

The lactic acid bacteria may be those belonging to the genus *Streptococcus, Lactococcus, Lactobacillus, Bifidobacterium*, or the like, with *Lactobacillus* being the most preferred. More specifically, *Lactobacillus bulgaricus, Lactobacillus helveticus, Lactobacillus casei, Lactobacillus acidophilus*, and *Lactobacillus fermentum* may be used, with *Lactobacillus helveticus* being the most preferred.

It is preferred to use a strain of *Lactobacillus helveticus* having high extracellular proteinase activity. For example, strains having a U/OD590 value of not lower than 400 are preferred, as measured in accordance with the method of Yamamoto et al. (Yamamoto N. et al., J. Biochem. (1993) 114, 740) based on the method of Twining et al. (Twining, S., Anal. Biochem. 143 3410 (1984)). Specifically, strains of *Lactobacillus helveticus* having the following bacteriological properties may be used.

Bacteriological Properties
1. Morphological Properties
   1) Shape of cell: rod
   2) Motility: none
   3) Spore formation: none
   4) Gram stain: positive
2. Physiological Properties
   1) Catalase production: negative
   2) Indole production: negative
   3) Nitrate reduction: negative
   4) Aerobic growth: facultative anaerobic
   5) Formation of DL(−)lactic acid from glucose by homolactic fermentation without formation of gases
   6) Carbohydrate degradation:
      glucose: +
      lactose: +
      mannose: +
      fructose: +
      galactose: +
      sucrose: −
      maltose: −
      xylose: −
      rhamnose: −
      cellobiose: −
      trehalose: −
      melibiose: −
      raffinose: −
      stachyose: −
      mannitol: −
      sorbitol: −
      esculin: −
      salicin: −

An example of such preferred strains of *Lactobacillus helveticus* is *Lactobacillus helveticus* CM-4 (deposited at International Patent Organism Depositary, National Institute of Advanced Industrial Science and Technology, Tsukuba Central 6, 1-1-1 Higashi, Tsukuba-shi, Ibaraki, Japan, under accession number FERM BP-6060 on Aug. 15, 1997) (referred to as CM-4 hereinbelow). CM-4 has been deposited under the above-mentioned accession number under the Budapest Treaty on the International Recognition of the Deposit of Microorganisms for the Purposes of Patent Procedure, and has already been patented.

The fermented milk whey may be obtained by adding a fermented milk starter containing lactic acid bacteria to milk, suitably selecting fermentation conditions, such as temperature, and fermenting the milk under the selected conditions.

The fermented milk whey as an active component, may be obtained by separating whey from the resulting fermented milk through an ordinary separation process, such as centrifugation or filtration. The fermented milk per se without separation, or separated whey may be used with or without suitable fractionation, concentration, purification, or the like, or the whey or its concentrate may be powdered by lyophilization or spray drying.

The lactic acid bacteria are preferably in the form of a pre-cultured starter having sufficiently high activity. The initial cell count may preferably be about $10^5$-$10^9$ cells/ml.

The fermented milk whey as an active component may also be obtained by cofermentation with lactic acid bacteria and a yeast, for improved flavor and palatability, when the fermented milk whey is to be used in functional food and beverage, such as foods for specified health uses, or in functional food and beverage claiming the effect of promoting epidermal keratinization. The strain of the yeast is not particularly limited, and may preferably be, for example, yeast of the genus *Saccharomyces*, such as *Saccharomyces cerevisiae*. The content of the yeast may suitably be selected depending on the purpose.

The starting material milk may be, for example, animal milk, such as cow's milk, horse's milk, sheep's milk, or goat's milk; vegetable milk, such as soybean milk; or processed milk thereof, such as skim milk, reconstituted milk, powdered milk, or condensed milk. Among these, cow's milk, soybean milk, and processed milk thereof are preferred, with cow's milk and its processed milk being particularly preferred.

The solid content of the milk is not particularly limited, and, for example, for skim milk, the solid-non-fat content may usually be about 3 to 15 wt %, and may be 6 to 15 wt % in the light of productivity.

The fermentation may be performed usually by static or stirred culture, for example at 25 to 45° C., preferably 30 to 45° C., for 3 to 72 hours, preferably 12 to 36 hours, and the fermentation may be terminated when the lactic acid acidity reaches 1.5 or higher.

The epidermal differentiation and keratinization promoter according to the present invention may optionally contain, in addition to the active component fermented milk whey, other conventional components having a promotive effect on epidermal differentiation and keratinization, and various additives, such as excipients, depending on its form.

The essential active component of the epidermal differentiation and keratinization promoter according to the present invention is the fermented milk whey, and its oral dosage may suitably be selected so that a desired effect may be achieved, taking into consideration of the duration of intake, continuity, or the like factors. The daily dose is usually 1 to 1000 ml of the fermented milk whey per person, preferably 10 to 200 ml per person.

The epidermal differentiation and keratinization promoter according to the present invention may be taken even after the symptoms of parakeratosis are developed, or in the seasons to prevent such symptoms, either continuously daily or intermittently.

The functional food and beverage of the present invention are food and beverage containing the present epidermal differentiation and keratinization promoter, and may be provided, for example, as food for specific health uses that claims prevention or improvement with regard to promotion of epidermal keratinization, or as functional food and beverage claiming an effect of promoting epidermal keratinization.

The present functional food and beverage may optionally contain additives, such as sugars, proteins, lipids, vitamins, minerals, flavoring agents, or mixtures thereof. Further, the milk components from which the fermented milk whey is separated, may also be contained.

In the functional food and beverage of the present invention, the content of the present epidermal differentiation and keratinization promoter may suitably be selected depending on the form or kind of the food and beverage. The content may suitably be selected also depending on the continuity of intake of the functional food and beverage or the like factors, and is not particularly limited. A suitable content may be usually 0.1 to 100 wt %, preferably 10 to 90 wt % in terms of the active component fermented milk whey.

The functional food and beverage may be in the form of, for example, fermented milk products, such as yogurt or lactic acid bacteria beverage, various processed food and beverage containing the fermented milk whey or a concentrate thereof, dry powders, tablets, capsules, granules, or the like.

The dose and the timing of administration of the functional food and beverage of the present invention are not particularly limited, and it is preferred to take the functional food and beverage in such an amount that the above-mentioned dose of the active component is generally achieved. For example, the present functional food and beverage may be taken continuously or intermittently before or after exposure to the environment that calls for promotion of epidermal keratinization.

EXAMPLES

The present invention will now be explained in more detail with reference to the examples, which are illustrative only and do not intend to limit the present invention.

Example 1

A milk medium composed of skim milk with a 9 wt % solid content was inoculated with 3% of CM-4 starter (cell count: $5 \times 10^8$ cells/mL), and fermented under static conditions at 37° C. for 24 hours to obtain a fermented milk. The fermented milk was centrifuged at 12000 G for 20 minutes, and the precipitate was removed to thereby obtain a fermented milk whey. Using the obtained fermented milk whey, the following tests were conducted.

<Test for Evaluation of Differentiation Promotive Effect and Cytotoxicity Test>
1) Method
(a) Cultured Epidermal Cells and Medium Commercially available (from KURABO INDUSTRIES LTD.) normal human epidermal cells and a culture medium (Humedia-KG2) were used.
(b) Cell Culture The cell count of the normal human epidermal cells was adjusted with the above medium to $5.652 \times 10^4$ cells/mL. 60 mm culture dishes were each seeded with 5 mL of the cells, and cultured under static conditions at 37° C. for 24 hours in the atmosphere of 95% (V/V) air –5% (V/V) carbon dioxide gas. Then the medium was replaced with a same medium containing the fermented milk whey at the final concentration of 0.03, 0.1, 0.3, or 1%, or purified water as a control, and further fermented under static conditions for 24 hours. On the other hand, for a time course analysis, the medium was replaced with a same medium containing the fermented milk whey at the final concentration of 1%, and further fermented under static conditions for 0, 1, 2, 4, 6, or 8 days.

(c) Analysis of Differentiation Marker Expression by Immuno-Staining

Following the 24-hour culture in the presence/absence of the 1% fermented milk whey in above paragraph (b), the cells were fixed with 4% paraformaldehyde-PBS, and blocked with 10% rabbit serum in PBS. Mouse anti-cytokeratin 10 antibody (manufactured by Dako) or mouse anti-involucrin antibody (manufactured by YLEM) was reacted at room temperature for 1 hour. Then the cells were washed with PBS, and reacted with peroxidase-labeled rabbit anti-mouse immunoglobulin antibody (manufactured by Dako) at room temperature for 30 minutes. The cells were washed again with PBS, and subjected to coloration using DAB Substrate-Chromogen System (manufactured by Dako). The results are shown in FIG. 1.

In FIG. 1, micrograph (a) shows the result of observation of Keratin 10 expression in the absence of the fermented milk whey, and micrograph (b) shows the corresponding result in the presence of the fermented milk whey at the final concentration of 1%. Micrograph (c) shows the result of observation of Involucrin expression in the absence of the fermented milk whey, and micrograph (d) shows the corresponding result in the presence of the fermented milk whey at the final concentration of 1%.

(d) Analysis of Differentiation Marker Expression by Real-Time RT-PCR

Figure 4:
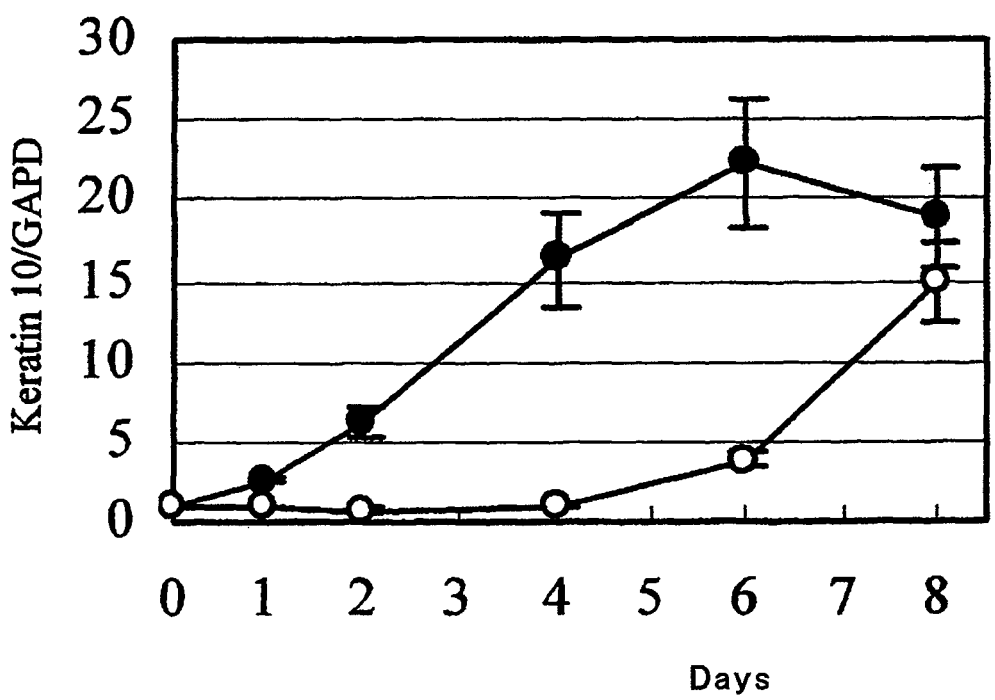
FIG. 4 is a graph showing the change in expression of differentiation marker (keratin 10) against time, demonstrated in Example 1.
Figure 5:
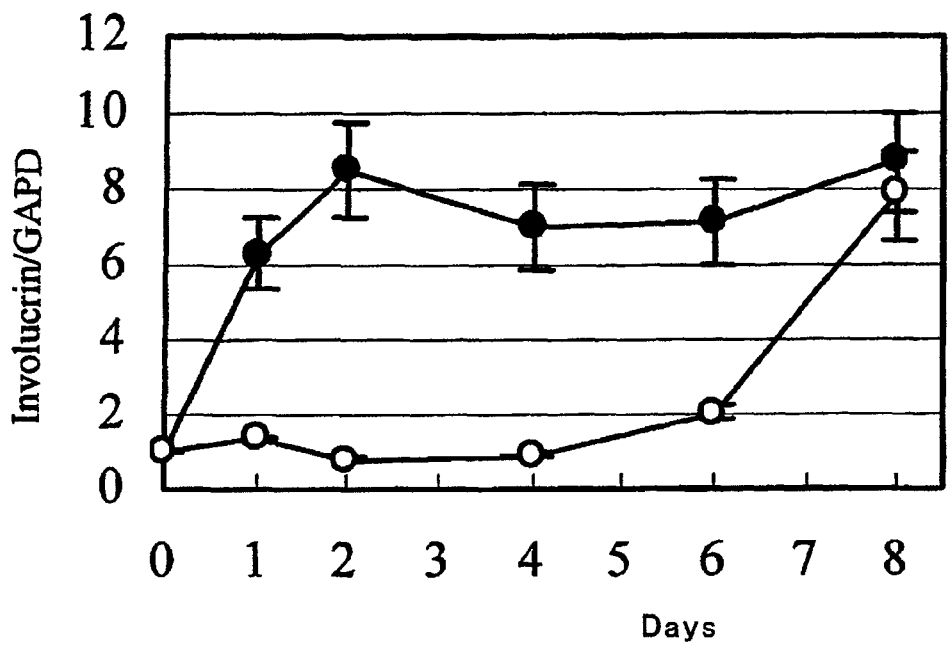
FIG. 5 is a graph showing the change in expression of differentiation marker (involucrin) against time, demonstrated in Example 1.

Following the 24-hour culture in the presence/absence of the fermented milk whey at various concentrations, and the culture for the time course analysis, both in above paragraph (b), the culture supernatant was aspirated away, and the remaining cells were washed twice with Hepes buffer. Using RNeasy Mini Kit (manufactured by QIAGEN), the total RNAs were extracted from the cells. 1 ng of the extracted total RNAs was subjected to Real-time RT-PCT using One Step SYBR RT-PCR Kit (trade name, manufactured by TaKaRa) in Smart Cycler II System (manufactured by CEPHEID) in accordance with its protocol using the primers shown in Table 1, to quantify the expressions of Keratin 10 mRNA, Involucrin mRNA, and glyceraldehyde 3 phosphate dehydrogenase (GAPD) mRNA. The obtained expressions were standardized by dividing the same by the expression of GAPD mRNA, which is believed to be expressed in the same amount in any cells, and the obtained values were expressed in relative values with respect to the value obtained for 0% concentration of the fermented milk whey in the medium in the above paragraph (b) (control), which was taken as 1. The results are shown in FIGS. 2 to 5. In FIGS. 4 and 5, the black circles indicate the results in the presence of the fermented milk whey, and the white circles indicate the results in the absence of the fermented milk whey.

(e) Cytotoxicity Test

Figure 6:
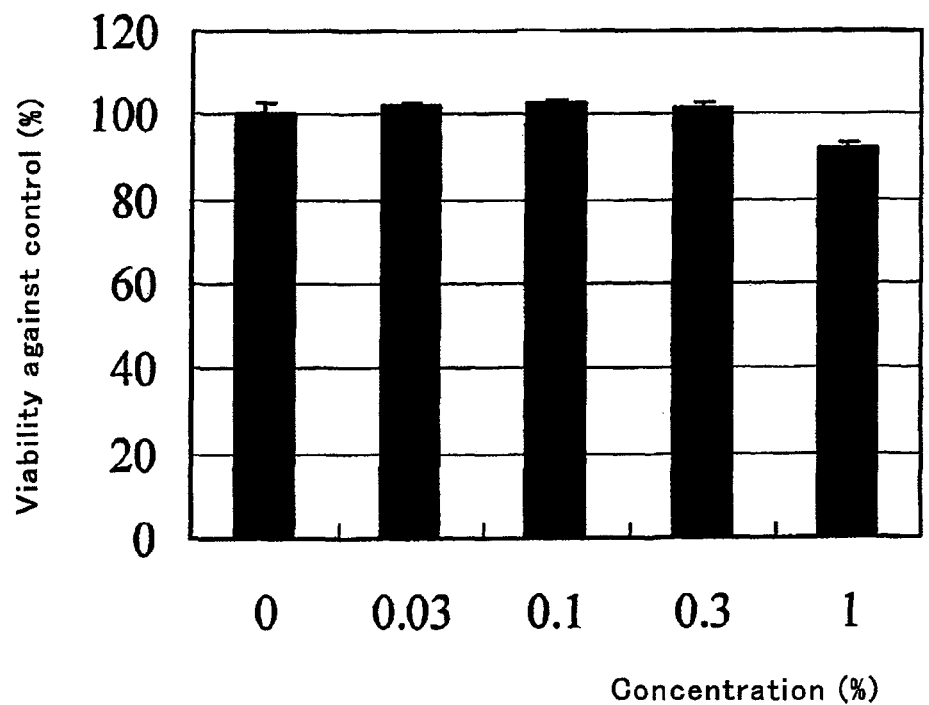
FIG. 6 is a graph showing the results of the cytotoxicity test conducted in Example 1.

Normal human epidermal cells were cultured in the presence of the sample at various concentrations for 48 hours in the same way as in above paragraph (b), and subjected to the cytotoxicity test using the Alamar Blue reagent (manufactured by NACALAI TESQUE, INC.) in accordance with its protocol. The results are shown in FIG. 6.

TABLE 1

| Gene | Sequence (5' -> 3') | |
|---|---|---|
| GAPDH | 5' primer GCACCGTCAAGGCTGAGAAC | (SEQ ID NO: 1) |
| | 3' primer ATGGTGGTGAAGACGCCAGT | (SEQ ID NO: 2) |
| Keratin 10 | 5' primer GGATGAGCTGACCCTGACCAA | (SEQ ID NO: 3) |
| | 3' primer GCAGCATTCATTTCCACATTCAC | (SEQ ID NO: 4) |

TABLE 1-continued

| Gene | Sequence (5' -> 3') | |
|---|---|---|
| Involucrin | 5' primer TAACCACCCGCAGTGTAAAG | (SEQ ID NO: 5) |
| | 3' primer CACCTAGCGGACCCGAAATAAG | (SEQ ID NO: 6) |

From FIG. 1, it is seen that expression of Keratin 10 and Involucrin was not observed in the absence of the fermented milk whey, but was observed to be promoted by addition of the fermented milk whey.

Figure 2:
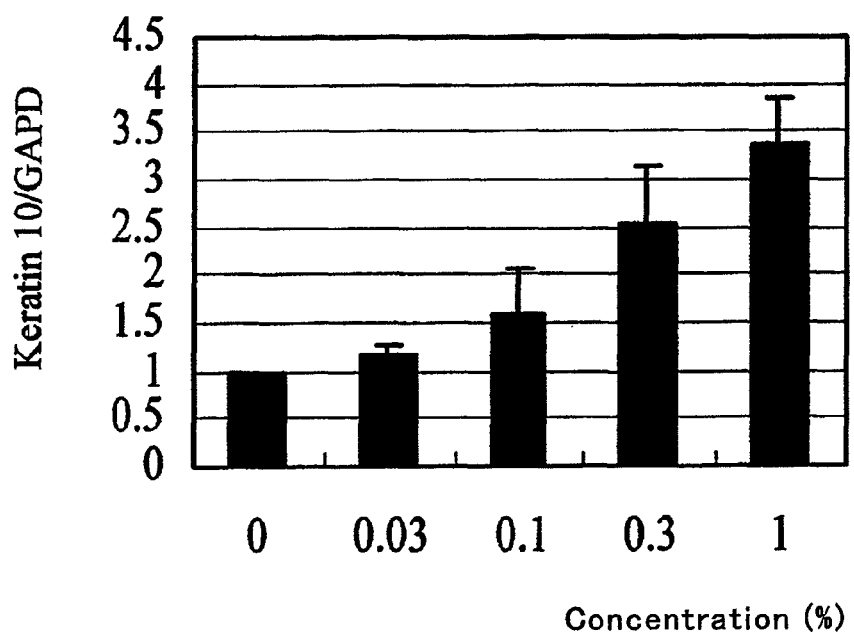
FIG. 2 is a graph showing the keratin 10 expression promotive effect at the mRNA level, demonstrated in Example 1.
Figure 3:
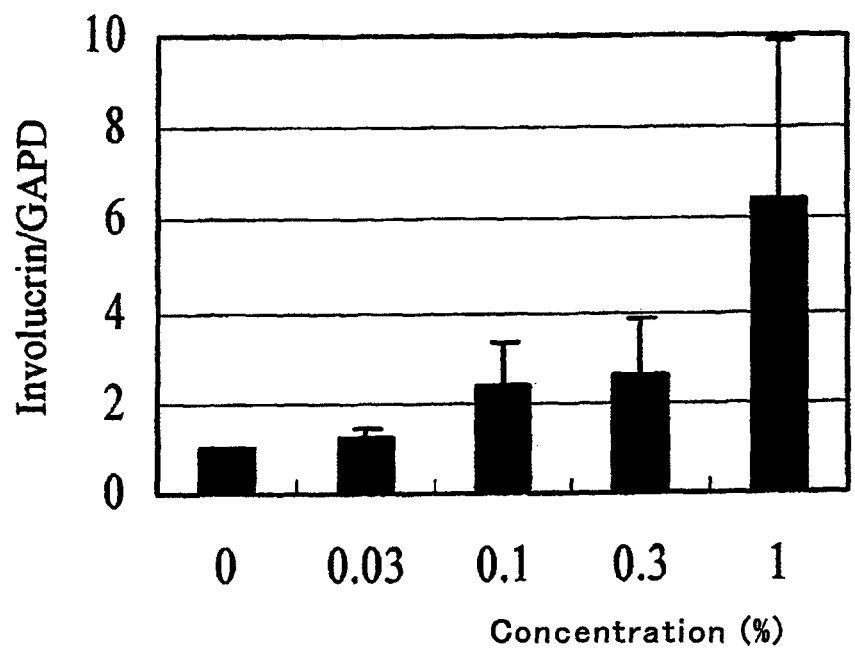
FIG. 3 is a graph showing the involucrin expression promotive effect at the mRNA level, demonstrated in Example 1.

From FIGS. 2 and 3, it is seen that expressions of Keratin 10 and Involucrin increase in dependence on the amount of the fermented milk whey added.

From FIGS. 4 and 5, it is demonstrated that the fermented milk whey promoted expression of the epidermal differentiation markers, Keratin 10 and Involucrin.

From FIG. 6, it is seen that no cytotoxicity was observed in adding the fermented milk whey.

Example 2

For making the fermented milk whey prepared in Example 1 suitable for drinking, 90 parts by mass of the fermented milk whey, 0.25 parts by mass of flavoring agents, 0.05 parts by mass of aspartame, and 9.70 parts by mass of water were mixed to prepare beverage containing fermented milk whey. The obtained beverage was subjected to the following evaluations.

<Evaluation of Change in Corneocyte Area by Oral Intake>

By adhesive tape stripping using a cellophane tape (manufactured by NICHIBAN CO., LTD.), corneocytes in the outermost layer on the left cheek were peeled, transferred to a glass slide, and fixed there. The fixed cells were stained with brilliant green-gentian violet (BG), and the image of the stained cells was captured on a computer. By analysis of the BG-stained image, the corneocyte area was determined.

The above evaluation test was conducted on 16 male panels of 24 to 43 years of age with the average age of 29.4 years old. The test was first conducted before the intake of the sample, and the average of the values for the panels was obtained. Next, the panels were given 150 g per day of the beverage containing fermented milk whey daily for 9 weeks, the evaluation test was conducted in the same way after the 9 weeks, and the average of the values for the panels was obtained. The results are shown in Table 2.

TABLE 2

| Before Test Mean ± SD | After 9 weeks Mean ± SD |
|---|---|
| 419 ± 64 | 446 ± 38 |

From Table 2, it is seen that the corneocyte area was increased by 27 after 9 weeks of intake in the group which took the beverage containing fermented milk whey, which suggests that long-term intake of the beverage containing fermented milk whey promotes epidermal keratinization.

What is claimed is:

1. A method for promoting epidermal differentiation and keratinization comprising orally administering to a subject in need thereof an effective amount of fermented milk whey obtained by fermentation of milk with bacteria,
   wherein the subject in need of the promoting epidermal differentiation and keratinization is one who has developed parakeratosis or who has a history of previously developing parakeratosis due to change of the seasons or climate; and
   wherein the bacteria comprise lactic acid bacteria.

2. The method according to claim 1, wherein said lactic acid bacteria comprise *Lactobacillus helveticus*.

3. The method according to claim 2, wherein said *Lactobacillus helveticus* is *Lactobacillus helveticus* CM-4 (deposited at International Patent Organism Depositary, National Institute of Advanced Industrial Science and Technology under accession number FERM BP-6060).

4. The method according to claim 1, wherein said fermented milk whey is formulated into food or beverage.

5. A method for suppressing skin dryness or roughness comprising orally administering to a subject in need thereof an effective amount of fermented milk whey obtained by fermentation of milk with bacteria,
   wherein the subject in need of suppressing skin dryness or roughness is one who has developed parakeratosis or who has a history of previously developing parakeratosis due to change of the seasons or climate; and
   wherein the bacteria comprise *Lactobacillus helveticus*.

6. The method according to claim 5, wherein said *Lactobacillus helveticus* is *Lactobacillus helveticus* CM-4 (deposited at International Patent Organism Depositary, National Institute of Advanced Industrial Science and Technology under accession number FERM BP-6060).

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: 5' primer

<400> SEQUENCE: 1
gcaccgtcaa ggctgagaac                                        20

<210> SEQ ID NO 2
<211> LENGTH: 20
<212> TYPE: DNA
<213> ORGANISM: Artificial
<220> FEATURE:
<223> OTHER INFORMATION: 3' primer

<400> SEQUENCE: 2
atggtggtga agacgccagt                                        20

<210> SEQ ID NO 3
<211> LENGTH: 21
<212> TYPE: DNA
<213> ORGANISM: Artificial
<220> FEATURE:
<223> OTHER INFORMATION: 5' primer -continued

```
<400> SEQUENCE: 3
ggatgagctg accctgacca a                                                  21

<210> SEQ ID NO 4
<211> LENGTH: 23
<212> TYPE: DNA
<213> ORGANISM: Artificial
<220> FEATURE:
<223> OTHER INFORMATION: 3' primer

<400> SEQUENCE: 4
gcagcattca tttccacatt cac                                                23

<210> SEQ ID NO 5
<211> LENGTH: 20
<212> TYPE: DNA
<213> ORGANISM: Artificial
<220> FEATURE:
<223> OTHER INFORMATION: 5' primer

<400> SEQUENCE: 5
taaccacccg cagtgtaaag                                                    20

<210> SEQ ID NO 6
<211> LENGTH: 22
<212> TYPE: DNA
<213> ORGANISM: Artificial
<220> FEATURE:
<223> OTHER INFORMATION: 3' primer

<400> SEQUENCE: 6
cacctagcgg acccgaaata ag                                                 22
```